(12) United States Patent
Lewis et al.

(10) Patent No.: US 8,388,220 B2
(45) Date of Patent: Mar. 5, 2013

(54) LARGE ARRAY DIFFERENTIAL SCANNING CALORIMETER, DSC MEASURING UNIT

(75) Inventors: Edwin A. Lewis, Starkville, MS (US); Donald J. Russell, Orem, UT (US)

(73) Assignee: Waters Technologies Corporation, Milford, MA (US)

( * ) Notice: Subject to any disclaimer, the term of this patent is extended or adjusted under 35 U.S.C. 154(b) by 519 days.

(21) Appl. No.: 12/598,672

(22) PCT Filed: May 13, 2008

(86) PCT No.: PCT/US2008/063504
§ 371 (c)(1),
(2), (4) Date: Feb. 23, 2010

(87) PCT Pub. No.: WO2008/144297
PCT Pub. Date: Nov. 27, 2008

(65) Prior Publication Data
US 2010/0322281 A1    Dec. 23, 2010

Related U.S. Application Data

(60) Provisional application No. 60/930,463, filed on May 16, 2007.

(51) Int. Cl.
*G01K 17/00* (2006.01)
*G01N 25/00* (2006.01)

(52) U.S. Cl. ............... 374/34; 374/33; 374/45

(58) Field of Classification Search .......... 374/31, 374/33, 34, 43, 44, 45
See application file for complete search history.

(56) References Cited

U.S. PATENT DOCUMENTS

| | | | | |
|---|---|---|---|---|
| 5,806,979 A * | 9/1998 | Gschneidner et al. | .......... | 374/34 |
| 6,535,824 B1 * | 3/2003 | Mansky et al. | .......... | 374/49 |
| 6,742,926 B1 * | 6/2004 | Fesmire et al. | .......... | 374/45 |
| 7,641,384 B2 * | 1/2010 | Nakatani et al. | .......... | 374/31 |
| 7,677,795 B2 * | 3/2010 | Schick | .......... | 374/10 |
| 2002/0034210 A1 * | 3/2002 | Plotnikov et al. | .......... | 374/10 |
| 2003/0101006 A1 * | 5/2003 | Mansky et al. | .......... | 702/30 |
| 2003/0186453 A1 | 10/2003 | Bell et al. | | |
| 2005/0036536 A1 * | 2/2005 | Lewis | .......... | 374/2 |
| 2006/0159585 A1 * | 7/2006 | Torres et al. | .......... | 422/51 |
| 2010/0046573 A1 * | 2/2010 | Schick et al. | .......... | 374/11 |
| 2010/0322281 A1 * | 12/2010 | Lewis et al. | .......... | 374/34 |
| 2011/0286493 A1 * | 11/2011 | Torniainen et al. | .......... | 374/33 |

FOREIGN PATENT DOCUMENTS

| | | |
|---|---|---|
| JP | 2003315292 | 11/2003 |
| JP | 2006201169 | 8/2006 |
| WO | 9960356 | 11/1999 |
| WO | 03025528 | 3/2003 |

OTHER PUBLICATIONS

Japanese Office Action dated Jun. 26, 2012 in Japanese Patent Application No. 2010-508532 and English-Language Translation.

* cited by examiner

*Primary Examiner* — Yaritza Guadalupe-McCall

(57) ABSTRACT

Embodiments of the present invention feature a method and apparatus for an energetics-based approach to screen and to characterize binding interactions between potential therapeutic (or diagnostic) agents and unknown target molecules. The methods and apparatus detect the occurrence of these reactions, the strength of the binding interaction and possibly the rate at which these processes take place.

15 Claims, 12 Drawing Sheets

LARGE ARRAY DIFFERENTIAL SCANNING CALORIMETER, DSC MEASURING UNIT

This application claims benefit of and is a continuation of International Application No. PCT/US2008/063504, filed May 13, 2008 and designating the United States, which claims benefit of a priority from U.S. Provisional Patent Application No. 60/930,463, filed May 16, 2007.

CROSS REFERENCE TO RELATED APPLICATIONS

This application claims benefit of U.S. Provisional Application No. 60/930,463, filed May 16, 2007, the content of which is incorporated herein by reference.

BACKGROUND

Substantial effort and funding are currently being expended in the genomics and proteomics fields with the focus of much of this effort being the discovery of new therapeutic and diagnostic agents. These therapeutic and diagnostic agents may work at the DNA (or RNA) level, the field of genomics, or at the protein level, the field of proteomics. In either case, the activity of a therapeutic and/or diagnostic agent resides in the ability of the drug molecule to bind tightly to a specific target molecule and through this complex formation to alter the function of the target molecule.

Currently there are two prevailing approaches to evaluate how effectively a particular drug binds with a target molecule, such as a nucleic acid or protein: the structural approach and the functional approach. The structural approach is based on predicting the potential of binding interactions from knowledge of the 3-D structures of the interacting molecules. This geometric approach, which evaluates how well the target molecule and drug molecule might fit together, is used to minimize the number of potential drug molecules that should be studied in detail. The functional approach is based on measurement of the change in the biological function of a nucleic acid or protein in the presence of the therapeutic agent.

SUMMARY OF THE INVENTION

Embodiments of the present invention feature a method and apparatus for an energetics-based approach to screen and to characterize binding interactions between potential therapeutic (or diagnostic) agents and unknown target molecules. The methods and apparatus detect the occurrence of these reactions, the strength of the binding interaction and possibly the rate at which these processes take place.

The methods and device utilize an array of multiple sample cells, and corresponding sensors, thus being capable of high throughput energy detection would be desirable.

The present system also allows for the use of known robotics for the purpose of filling the trays; moving them in and out of the system; and having the sensors inserted into the samples.

The present system also utilizes sensor pins. The use of a sensor pin means that the liquid sample around it has a shorter thermal path to the sensor—which allows for faster heat transfers to and from liquid sample.

The present system also allows for the individual cells to be adequately sealed (e.g. so that none of the sample or solvent is evaporated or boiled out as temperatures rise). Specifically, the present system, because it utilizes the 96 well trays—which as noted above, often have protruding rims—is able to incorporate a sealing gasket. The sealing gasket helps maintain the integrity of the sample being tested.

DETAILED DESCRIPTION OF THE ILLUSTRATED EMBODIMENT(S)

Figure 1:
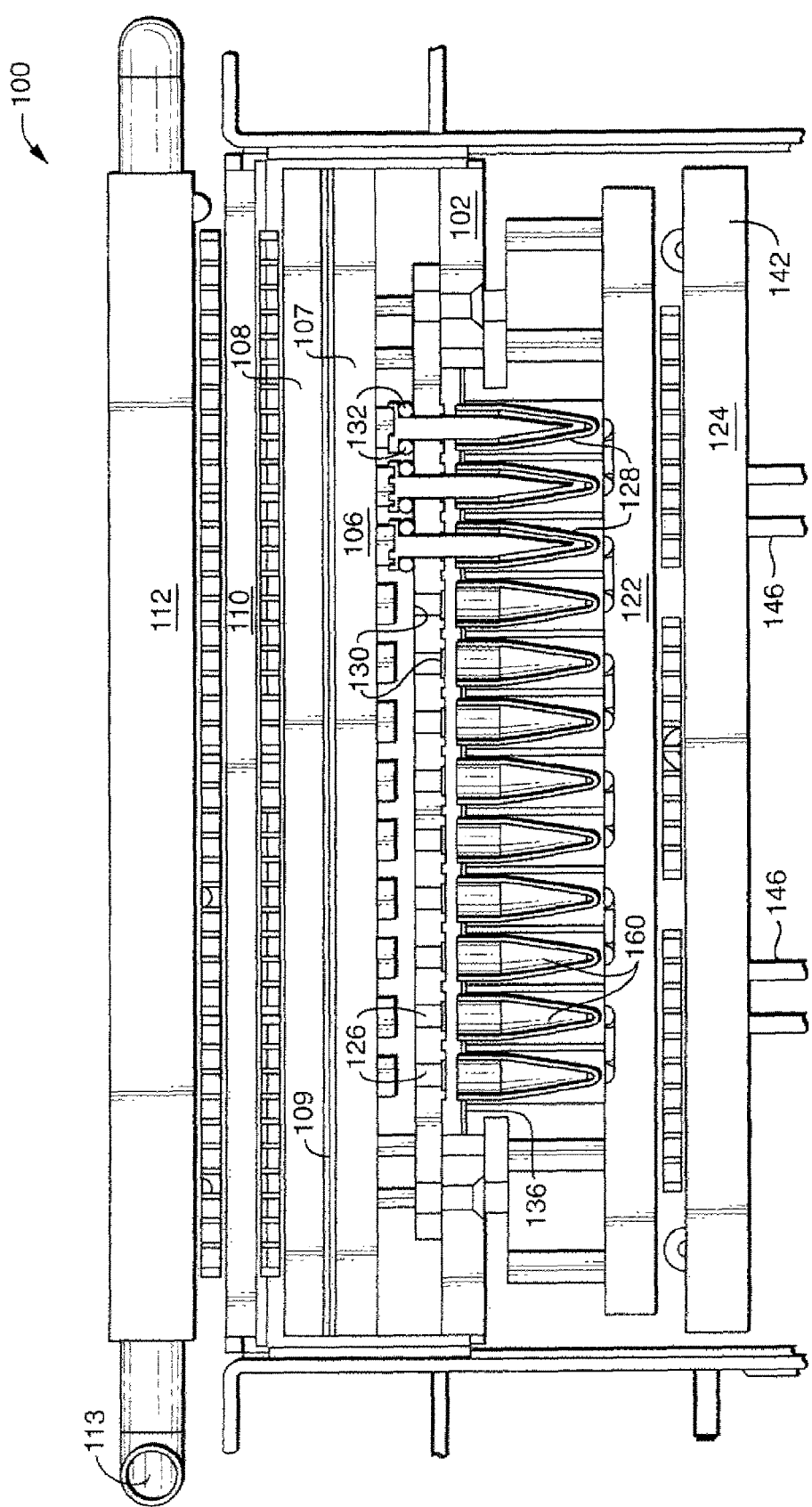
FIG. 1 shows a schematic diagram of a DSC measuring unit according to one embodiment of the present invention.

In FIG. 1, is shown a schematic diagram of a DCS measuring unit 100 according to one embodiment of the present invention. The measuring unit 100 includes a plurality of sensor pins 102. The sensor pins 102 in this embodiment are machined out of high purity copper. They are coated with a nickel plate, and a secondary impervious gold plating on the outside. As would be appreciated, it is desirable for the sensor pins to have high thermal conductivity and yet be chemically inert. Accordingly, the copper core, in this embodiment, can range from approximately 75% pure in an appropriate copper alloy to 99.99% pure; the nickel plate is 99.999% pure; and the gold is 99.999% pure. Nevertheless, as would be appreciated by one skilled in the art, different purity levels may, in some circumstances be adequate, and these purity levels are merely given as examples.

It is noted that the nickel prevents gold from amalgamating with the copper sensor pin body rendering it reactive. However, other materials that could serve this same function include, but are not limited to silver and platinum. Additionally, in certain embodiments, instead of the core of the sensor pin 102 being copper, it could be made of aluminum, silver, gold, platinum or any alloy or material with high thermal conductivity. Likewise, instead of utilizing gold as the outermost surface, the sensor pins could be plated with any inert conductive metal (e.g. silver or platinum) or be constructed from inert metals or alloys including but not limited to Hastelloy-C or tantalum.

The sensor pins 102 are designed to fit into 96 well plates commonly used in assay techniques. The exact diameter and length of the pin 102 will depend on the annulus of liquid that is desired in the well when filled. For example, in some analyses, a smaller liquid annulus will be desirable, consequently, a pin 102 that is longer, or has a larger diameter, or both would be appropriate. In some analyses a larger liquid annulus will be desirable, thus requiring a pin 102 that is shorter, has a smaller diameter, or both. Matching the correct pin 102 size to account for the type of analysis being done, is a function of sample well volume and geometry.

The sensor pins 102 are coupled to heat flow sensors 104. In this embodiment, the heat flow sensors 104 are Peltier sensors, or Seebeck devices. Semiconducting thermoelectric sensors (Peltier devices), are manufactured by a number of companies, including but not limited to Melcor, Ferrotech, and Micropelt. These manufacturers produce Peltier devices that are suitable for use as heat flow sensors in the present invention. However, as would be apparent to one skilled in the art, sensors could also be used. For example, other heat flow or temperature difference sensors that could be used in the present invention include, but are not limited to thermocouples, thermopiles, thermistors, and resistance temperature devices (RTDs).

In one embodiment, the use of thermopile sensors is contemplated. Because these types of sensors typically have lower sensitivity (Volts/Watt), modifications may also need to be made in the amplification components to account for the difference in sensitivity (as would be apparent one skilled in the art). Other types of sensors that could be incorporated into the present invention are RTD sensors (usually platinum or copper wound sensors) or semi-conducting thermister sensors (used in pairs). In short, any number of sensors that would be apparent to one skilled in the art could be incorporated into the present invention provided they are capable of measuring the temperature difference between sensor pin 102 and calorimeter block.

Referring again to the present embodiment containing Peltier sensors, the sensor pins 102 can be coupled to the sensors 104 in a variety of ways. For example, they can be soldered of glued to the sensors 104.

Figure 3:
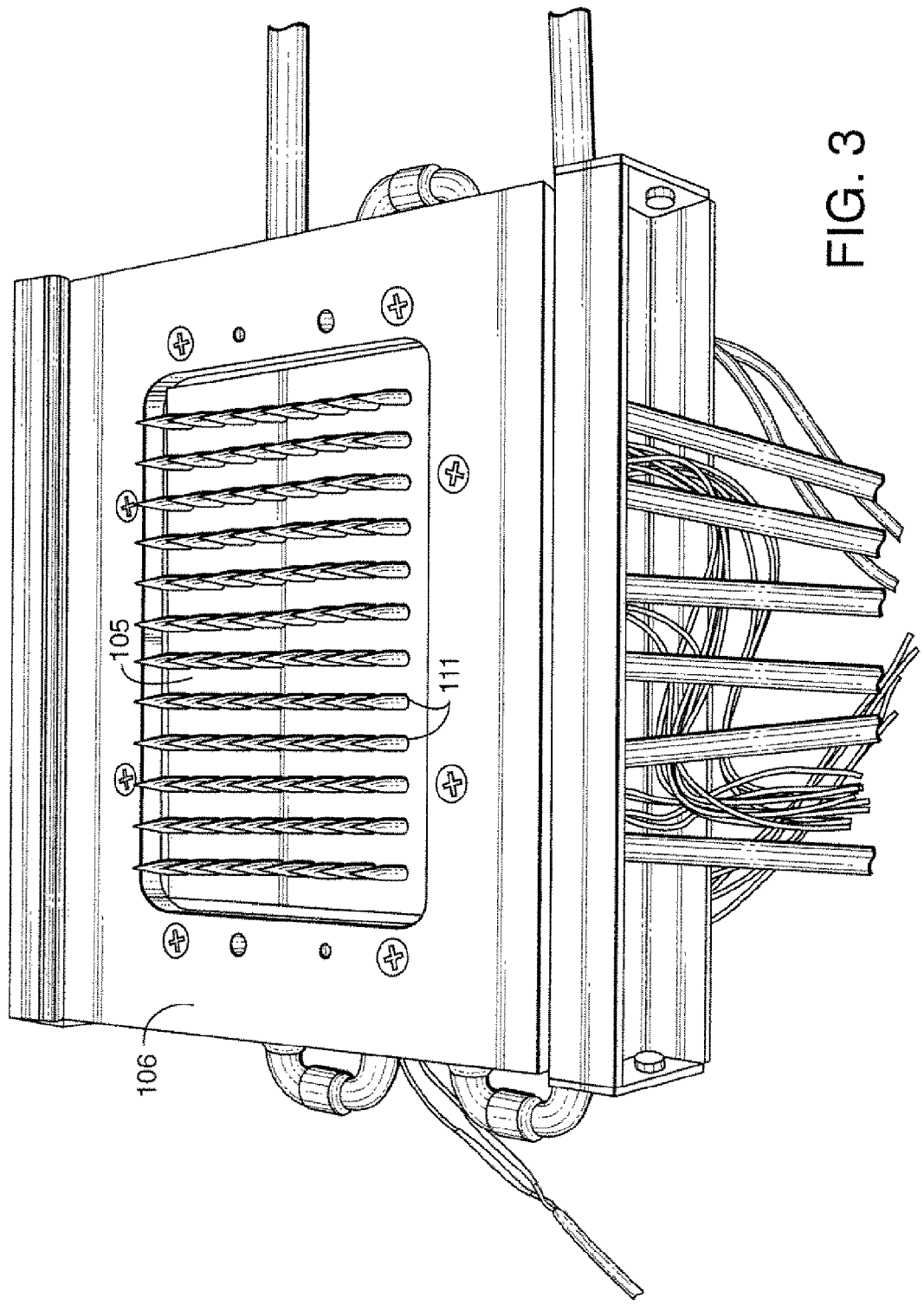
FIG. 3 shows a temperature controlled block assembly (before sensor placement) according to one embodiment of the present invention.
Figure 4:
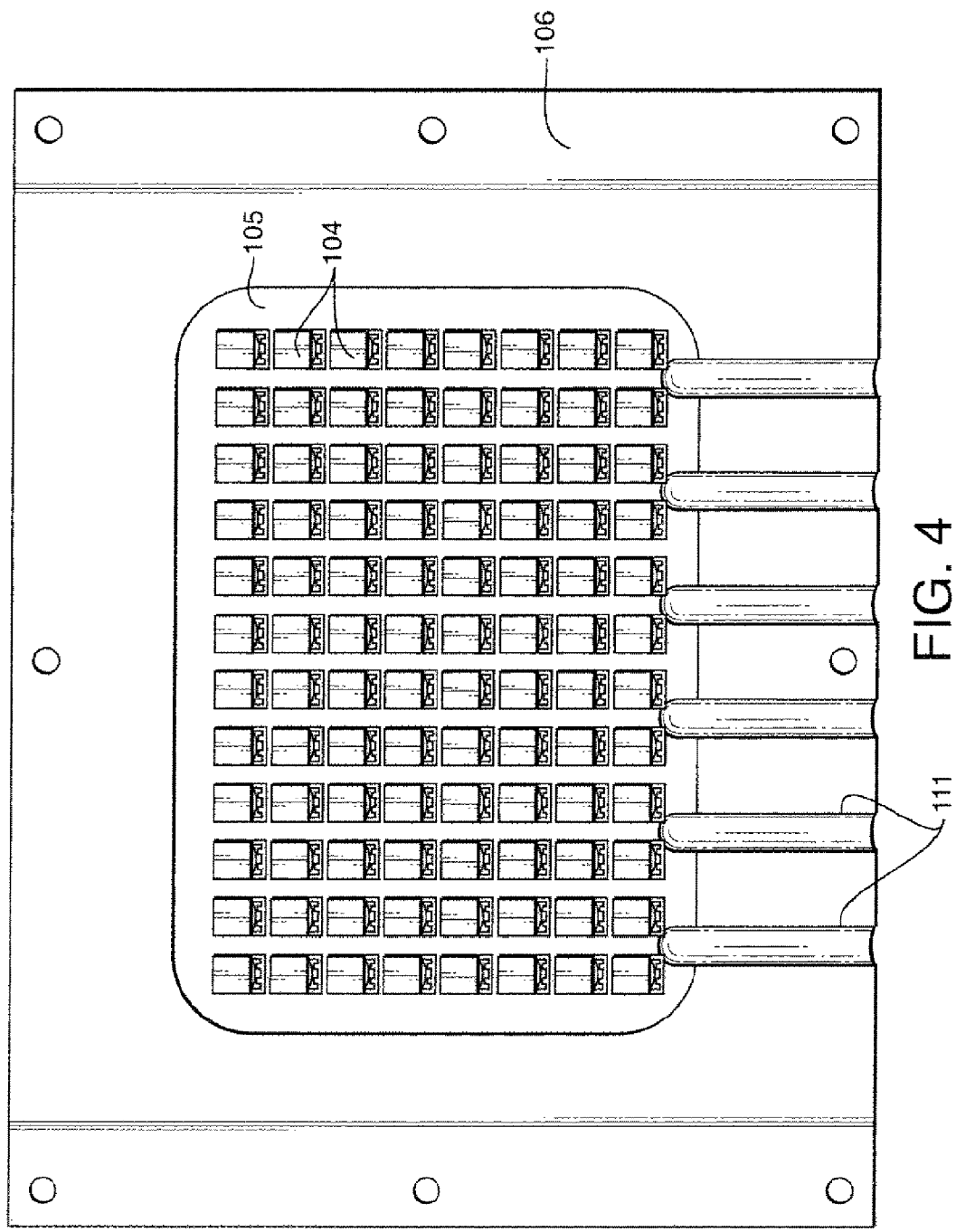
FIG. 4 shows a temperature controlled block assembly (after sensor placement) according to one embodiment of the present invention.
Figure 5:
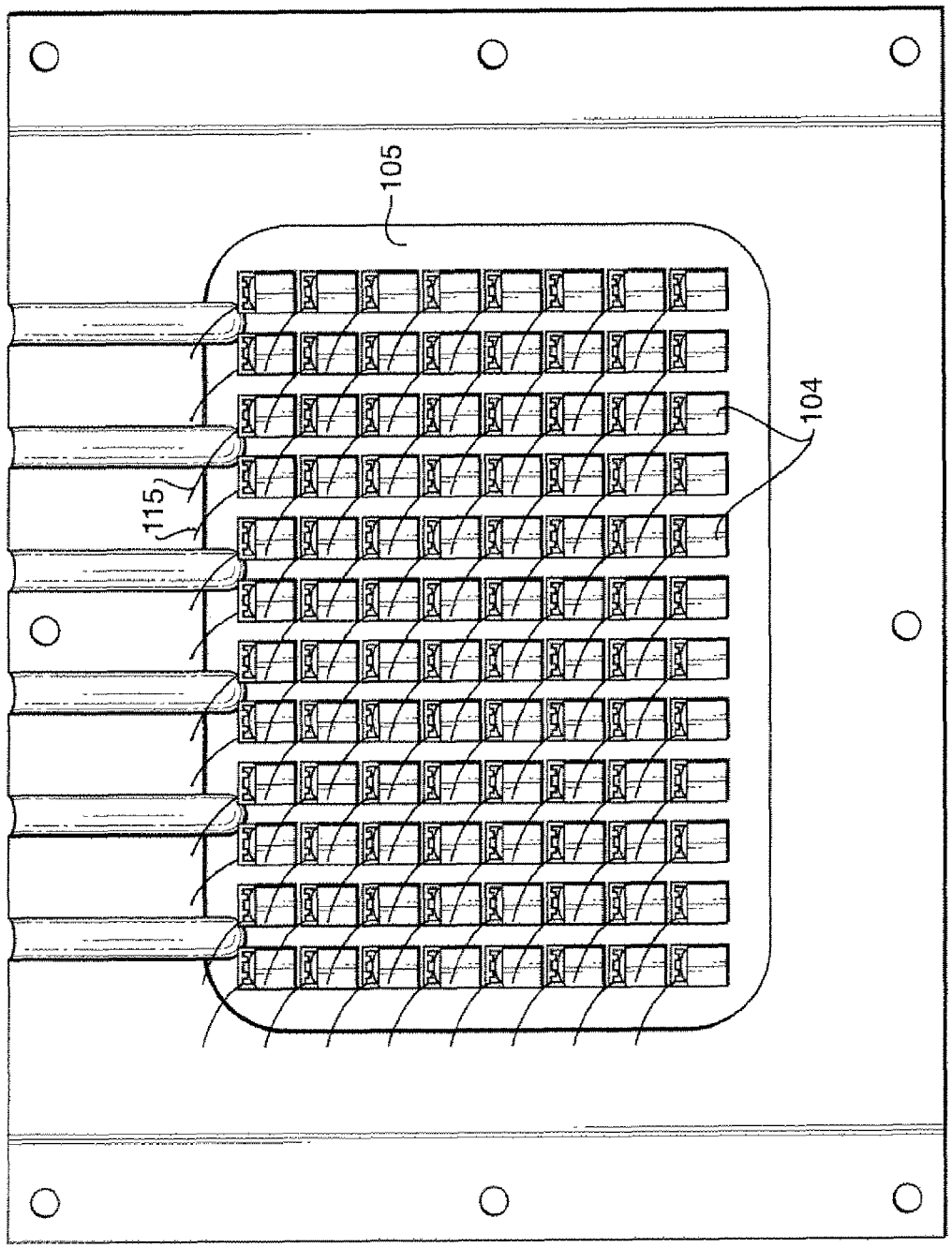
FIG. 5 shows a sensor array and wire connections according to one embodiment of the present invention.

The heat flow sensors 104 in this embodiment are coupled to a calorimeter block 106. As better seen in FIGS. 3-5, in this embodiment, the calorimeter block 106 is an aluminum piece having a recess 105 into which the sensors 104 are placed to correspond to the sensor pins 102—which in turn correspond to the wells in the 96 well plate 120. However, the calorimeter block 106 could be made from numerous other thermally conductive materials that would be apparent to one skilled in the art including, but not limited to, copper, gold and silver.

The calorimeter block 106 has two stages: stage I 108 and stage II 107. Between stage I and stage II is a thermal dampening material 109. The calorimeter block 106 is in thermal communication with a scan block 110 by virtue of one or more temperature control modules 116.

Thus, in this embodiment, the temperature of stage I is actively controlled, and the temperature of stage II is passively controlled. The thermal dampening materials 109 is a substance having a relatively low thermal conductivity. For example, the dampening material 109 could be a thin layer of aluminum sandwiched between thin layers of silicone rubber. The thermal gradient or temperature fluctuation dampening material could also be a single layer of low thermal conductivity material (e.g. a thin sheet silicone rubber) or several thin layers of thermally conductive material (e.g. thin sheets of aluminum) sandwiched between several alternating layers of insulating (or low thermal conductivity) material (e.g. thin sheets of silicone rubber). Numerous other materials for the dampening material 109 would be apparent to one skilled in the art, provided they are capable of dampening or buffering temperature fluctuations or gradients in temperature by virtue of having comparatively lower thermal conductivity. For example, other dampening materials 19 include, but are not limited to plastics, glasses, insulating foams, glass fiber or ceramic insulting materials, and layers of trapped air.

The temperature control modules 116 are the means for secondary (or fine) control of the heating rate or scanning the temperature of the calorimeter. The temperature control modules 116 are high power semi conducting thermoelectric sensors (e.g. Peltier devices). Peltier devices are manufactured by a number of companies, including but not limited to Melcor, Ferrotech, and Micropelt. These manufacturers produce Peltier devices that are suitable for use as temperature control modules in the present invention. The temperature control modules 116 transfer some heat from the scan block 110 to Stage I 108 of the calorimetric block 106. The temperature control modules 116 also provide some additional heating power so that Stage I 108 of the calorimetric block 106 and the scan block 110 are at the same temperature ($\Delta T = T(108) - T(106) = 0$). The temperature control modules 116 could be replaced or substituted with other suitable heating devices including but not limited to resistive heating elements (e.g. coil or film heaters).

The scan block 110 is the calorimeter block reference temperature component and is constructed from a significant mass of a highly thermally conductive material having a large heat capacity. In the present embodiment, the scan block 110 is a thick aluminum plate. The scan block could be made from a number of other materials including but not limited to stainless steel, copper, silver, or gold. The scan block 110 is in thermal communication with one or more scan control modules 114. The scan control modules 114 are the primary (or course) means for controlling the heating rate or scanning the temperature of the calorimeter. The scan control modules 114 are high power semi conducting thermoelectric sensors (Peltier devices). Peltier devices are manufactured by a number of companies, including but not limited to Melcor, Ferrotech, and Micropelt. These manufacturers produce Peltier devices that are suitable for use as scan control modules in the present invention. The scan control modules 114 are able to heat the scan block 110 at a regular rate (e.g. increase 1 degree per minute). The scan control modules 114 could be replaced with other suitable heating devices including but not limited to resistive heating elements (e.g. coil or film heaters).

A heat sink 112 is placed substantially over the scan control modules 114 to provide a thermally stable environment in which the present system 100 can operate. In the present embodiment, the heat sink 112 is a large copper block through which coolant flows during instrument cool-down or rest cycles. The heat sink could be made from a number of other materials having high thermal conductivity and high heat capacity, including, but not limited to stainless steel, copper, silver, or gold. The coolant connections are made through a cooper heat exchange coil running through the heat sink 112 and the connecting coolant lines 113.

The heat sink 112 may be kept at a constant temperature, e.g. at or near room temperature, or allowed to float in temperature. The large heat capacity of the heat sink and its starting temperature as controlled by the flowing coolant allow the heat sink to serve as a reference point in controlling the temperature of the calorimeter and the rate at which the calorimeter scans up in temperature. In the present embodiment, a substantially constant temperature is maintained by a coolant line 113 that runs through the heat sink 112 (also see FIG. 11). The coolant can be water, or numerous other fluids that are capable of transferring heat, including, but not limited to other heat exchange fluids for example antifreeze, and oil.

It is also noted that the heat sink 112 could be maintained at the desired temperature by other means (besides a coolant line 113), including, but not limited to a high surface area or finned construction with fans to dissipate heat from the finned heat sink to the environment.

Over the well plate 120 is placed a well seal gasket 118. The well seal gasket 118 is a low durometer silicone sheet material. The well sealing mat or gasket could be made from a number of materials including but not limited to viton, Teflon, neoprene or other inert non-porous soft gasket materials. The well seal gasket 118 includes one or more channels 126 that correspond to the individual wells 128 in the 96 well plate 120. One or more protective membranes 130 are positioned over the channels 126. As the individual wells 128 are raised up, the sensor pins 102 puncture through the membranes 130, such that the environment in which the pins 102 are sensing is thermally protected to the fullest extent possible. The membranes 130 also help prevent cross-contamination of the samples through splashing.

The well seal gasket 118 also serves the secondary function of cushioning the 96 well plate 120 as it is raised to insert the sensor pins 102. This cushioning helps prevent crushing of the 96 well plate 120. To further cushion the 96 well plate 120, individual sensor gaskets 132 could also be inserted around the sensor pins 102.

Figure 2:
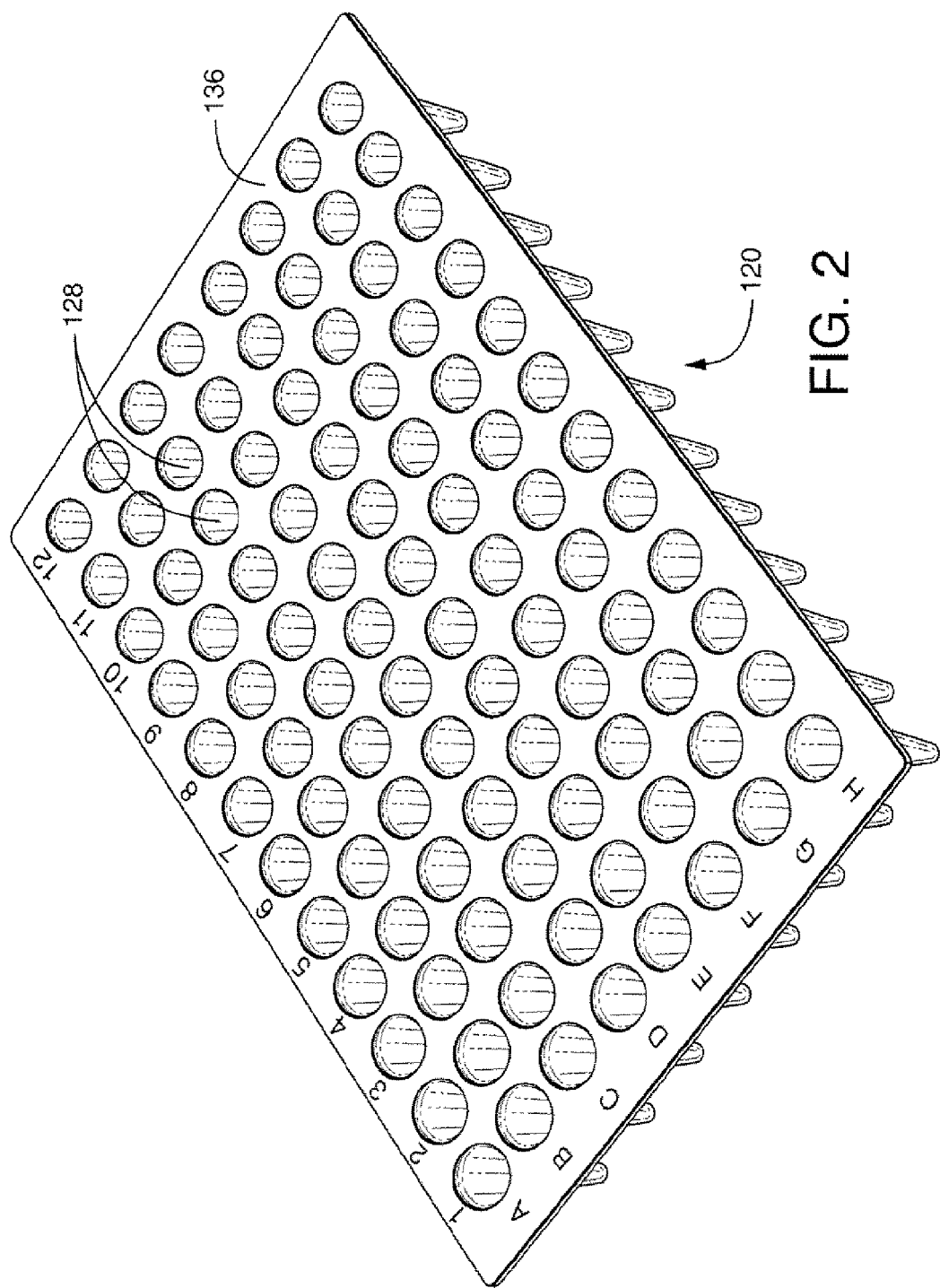
FIG. 2 shows a disposable well sample plate according to one embodiment of the present invention.
Figure 9:
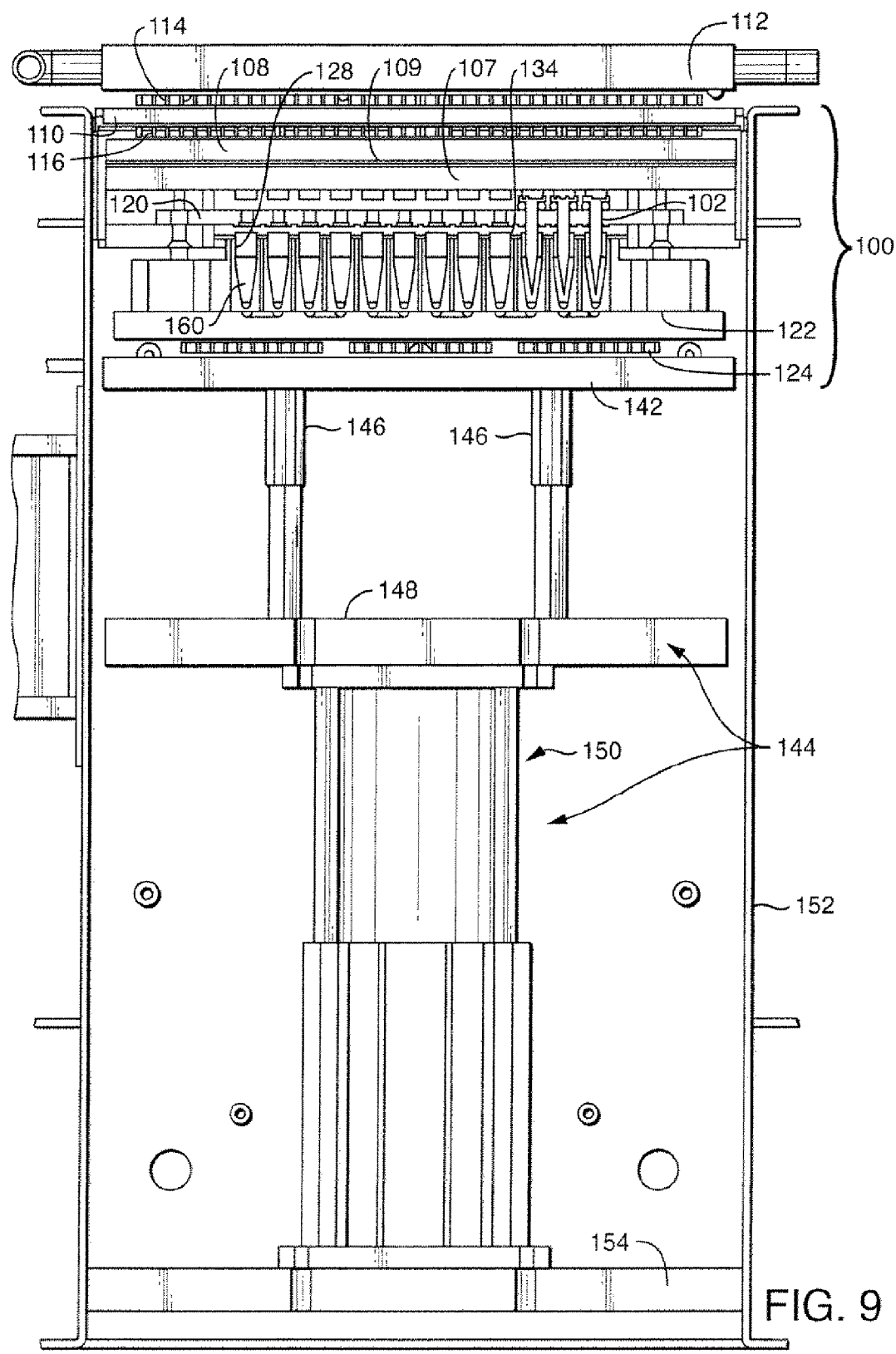
FIG. 9 shows the lift assembly according to one embodiment of the present invention.

It is noted that, in the present embodiment, the 96 well plate 120 is raised into communication with the sensor pins 102. However, in certain embodiments, the well plate 120 could be stationary and pins lowered. Located below the well plate 120 is an adiabatic shield 122. The adiabatic shield provides a temperature controlled environment surround the sample wells. The adiabatic shield is controlled to have the same temperature as the calorimeter blocks 106 and 108 and in the present embodiment is constructed from a block of aluminum into which a pattern of holes has been drilled to surround the sample wells of the plastic sample tray or 96 well plate 120. The adiabatic shield could be made from a number of other materials having high thermal conductivity and high heat capacity, including, but not limited to stainless steel, copper, silver, or gold. The adiabatic shield 122 is further shown in FIGS. 9 and 10. The adiabatic shield 122 includes one or more openings 134 that correspond to the wells 128 of the 96 well plate 120. Specifically, as best seen in FIG. 9, the 96 well plate 120 is placed upon the adiabatic shield 122. The wells 128 insert into the openings 134, and the top surface 136 (FIG. 2) of the 96 well plate 120 lies substantially flat against the top surface 138 (FIG. 10) of the adiabatic shield 122.

The adiabatic shield 122 can be maintained at substantially the same temperature as the scan block 110. The temperature of the adiabatic shield 122 is controlled through one or more shield control modules 124. The shield control modules 124 are high power semi conducting thermoelectric sensors (e.g. Peltier devices). Peltier devices are manufactured by a number of companies, including but not limited to Melcor, Ferrotech, and Micropelt. These manufacturers produce Peltier devices that are suitable for use as shield control modules in the present invention. The shield control modules 124 are able to heat the adiabatic shield 122 at a regular rate (e.g. increase 1 degree per minute) and keeping track with the temperature of the calorimeter blocks 106 and 108. The shield control modules 124 could be replaced with other suitable heating devices including but not limited to resistive heating elements (e.g. coil or film heaters).

Figure 6:
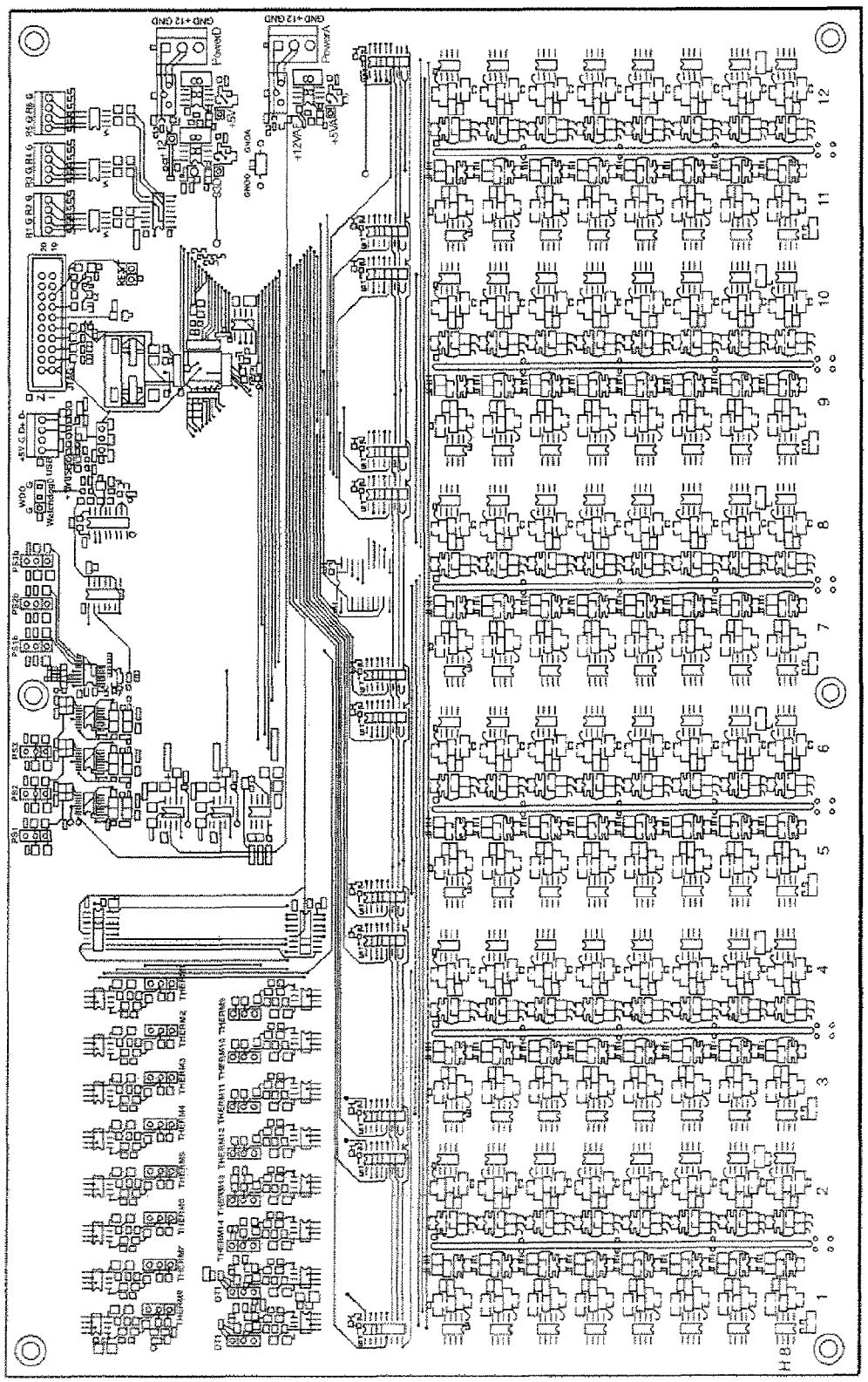
FIG. 6 shows an A/D and amplifier data acquisition board according to one embodiment of the present invention.
Figure 7:
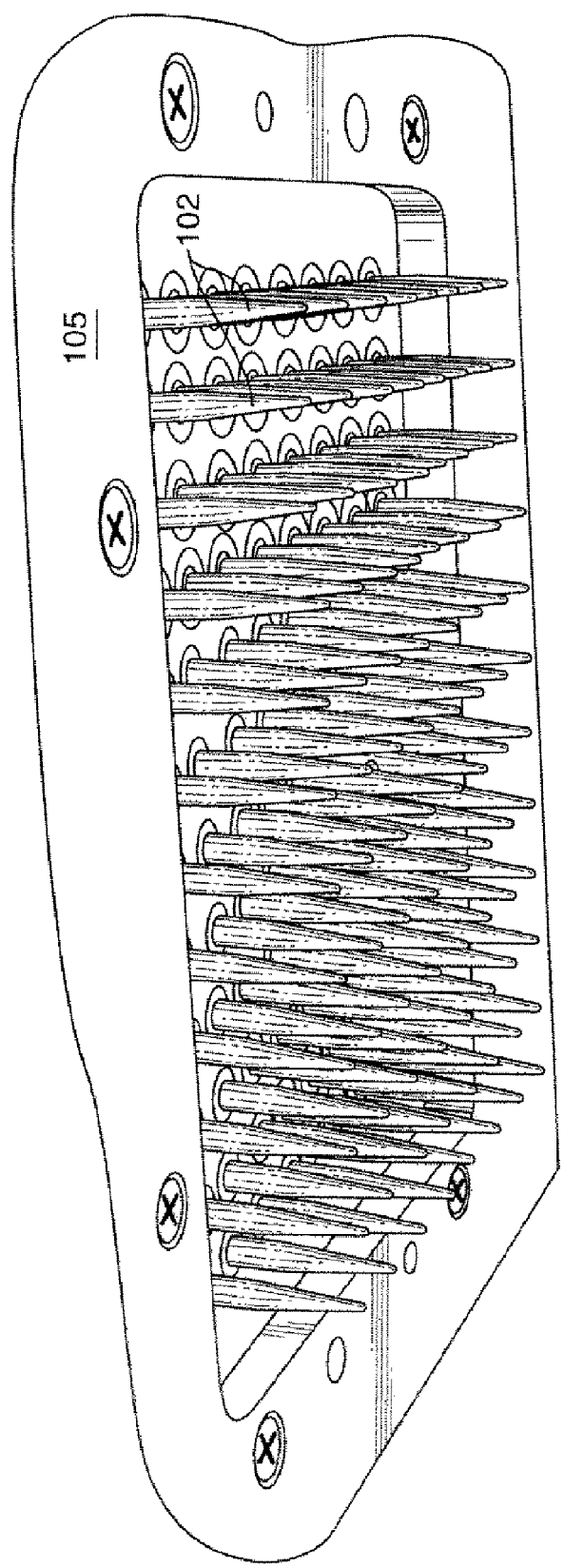
FIG. 7 shows a sensor pin array according to one embodiment of the present invention.
Figure 8:
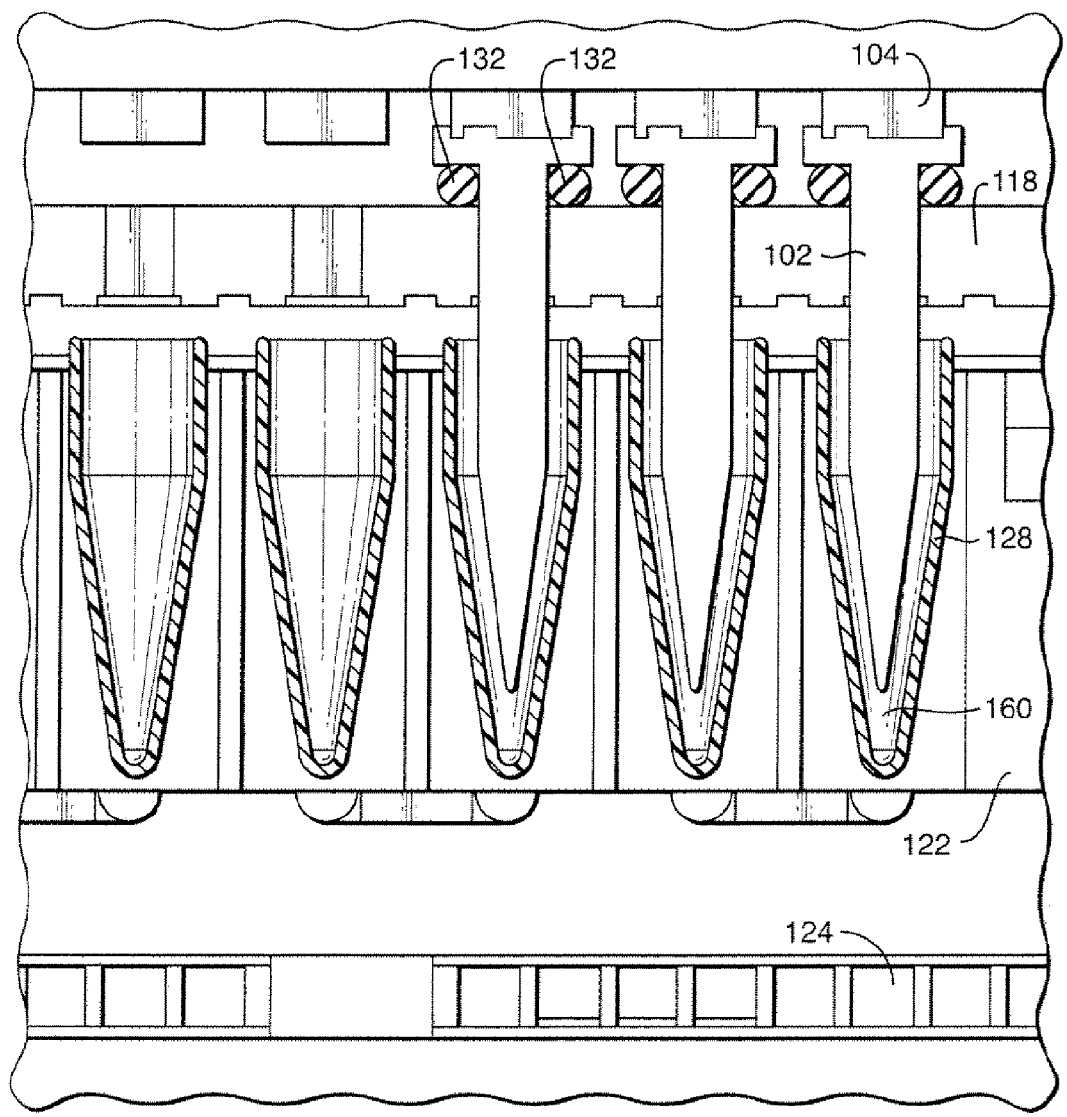
FIG. 8 shows a cross section of the sample wells and corresponding sensor pins, according to one embodiment of the present invention.

Sensor connecting wires 115 (FIG. 5) connect heat flow sensors 104 to an amplifier 117 (FIG. 6). The amplifier 117, as would be apparent to one skilled in the art, amplifies the 96 voltage signals developed by the 96 heat flow sensors 104 through wires 115. The amplified signals (from each of the 96 heat flow sensors) can then be collected/measured and processed. There are numerous off the shelf generic data acquisition (DAQ) cards and software programs available that could be applied for these purposes. Data acquisition and control is accomplished by use of a DAQ card with the appropriate Bus Type (e.g. USB/PCI/ISA), OS support (e.g. WIN), sampling rate (>1 kS/sec), and the requisite Analog Input (multichannel, minimum resolution 16 bits), Analog output, Digital I/O, counter timer, and triggering functions. One skilled in the art of calorimeter design, the acquisition of low level signals, and control of temperature using PID feedback algorithms, would be able to select a suitable off the shelf DAQ card, available from a number of manufacturers, including, but not limited to DataTranslation, IOTech, Microstar Laboratories, National Instruments, Sensoray, or Signatec. This processed information can then be transmitted to a personal computer 140 (FIG. 12), which then translates the processed signal into readable data. Suitable DAQ software is available from each of the DAQ card manufacturers (some are card specific). Suitable DAQ programs, include, but are not limited to DASYLab, DAPTools, DAS Wizard, and Daq-ViewXL. DAQ functions include all of the obvious instrument control functions (e.g. timing, start, stop, seal pressure monitoring, lift activation and positioning, gas purge, cleaning cycling, temperature limits, temperature equilibration, temperature control, and logging the amplified sensor voltage signals as a function of temperature). Amplified voltages are converted into apparent excess heat capacities for each of the samples as a function of temperature. Data analysis in terms of instrument or sample baseline signal subtraction, plotting the raw or baseline data from each of the 96 data channels, plotting or monitoring various instrument control or check functions and fitting the data to the appropriate thermal stability or denaturation models for the reporting of physical chemical data consistent with various models for thermal denaturation and or ligand binding by proteins and nucleic acids is accomplished with an off the shelf software package, Cp-Calc from Calorimetry Sciences Corporation. Another off the shelf software package capable of performing the DSC thermodynamic analysis is available from Origin (Origin 7.0). Channels 111 (FIGS. 3 and 4) can also be included as a pathway through which the wires 115 can be thread.

Figure 10:
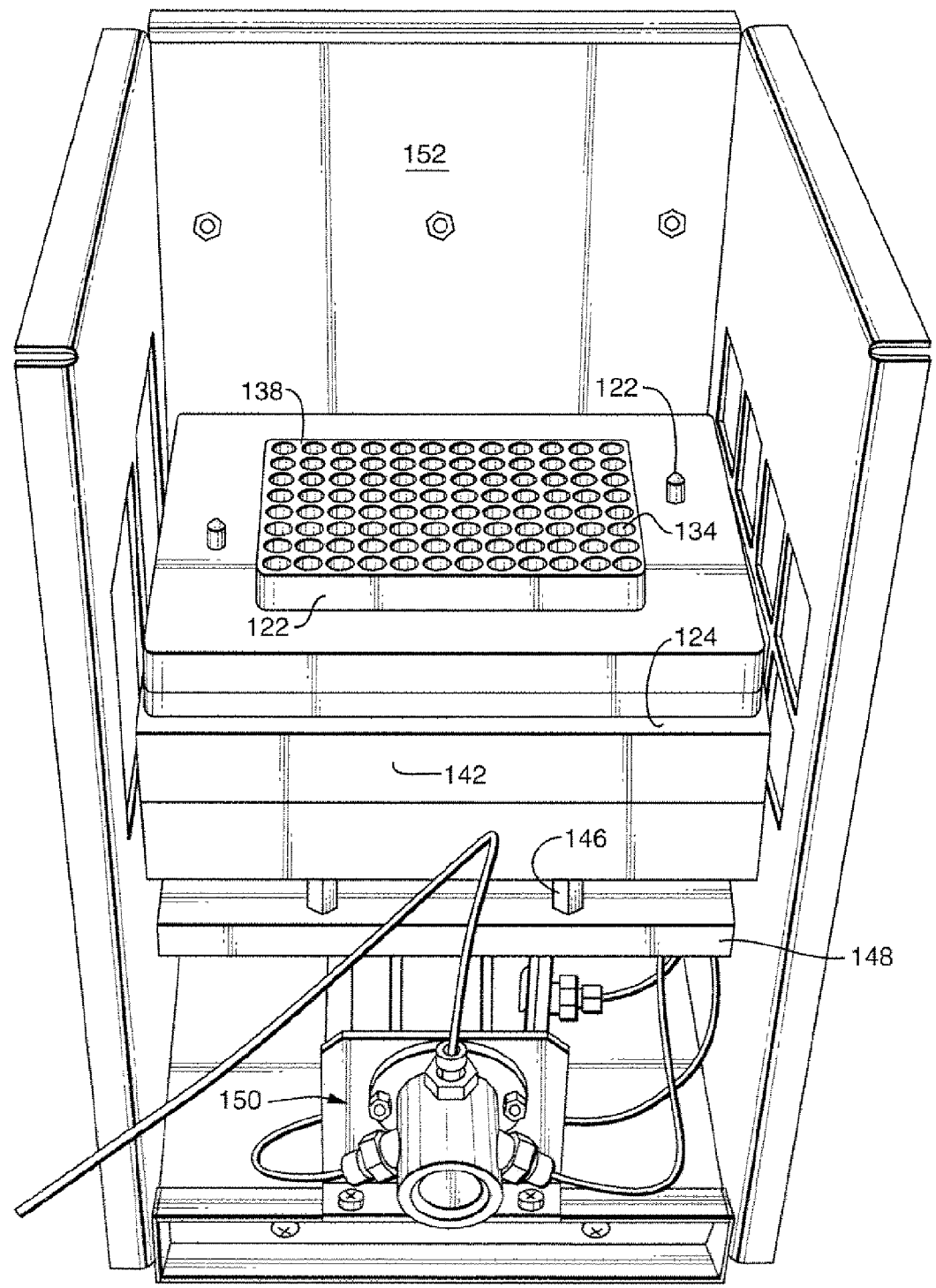
FIG. 10 shows the lower shield assembly according to one embodiment of the present invention.
Figure 11:
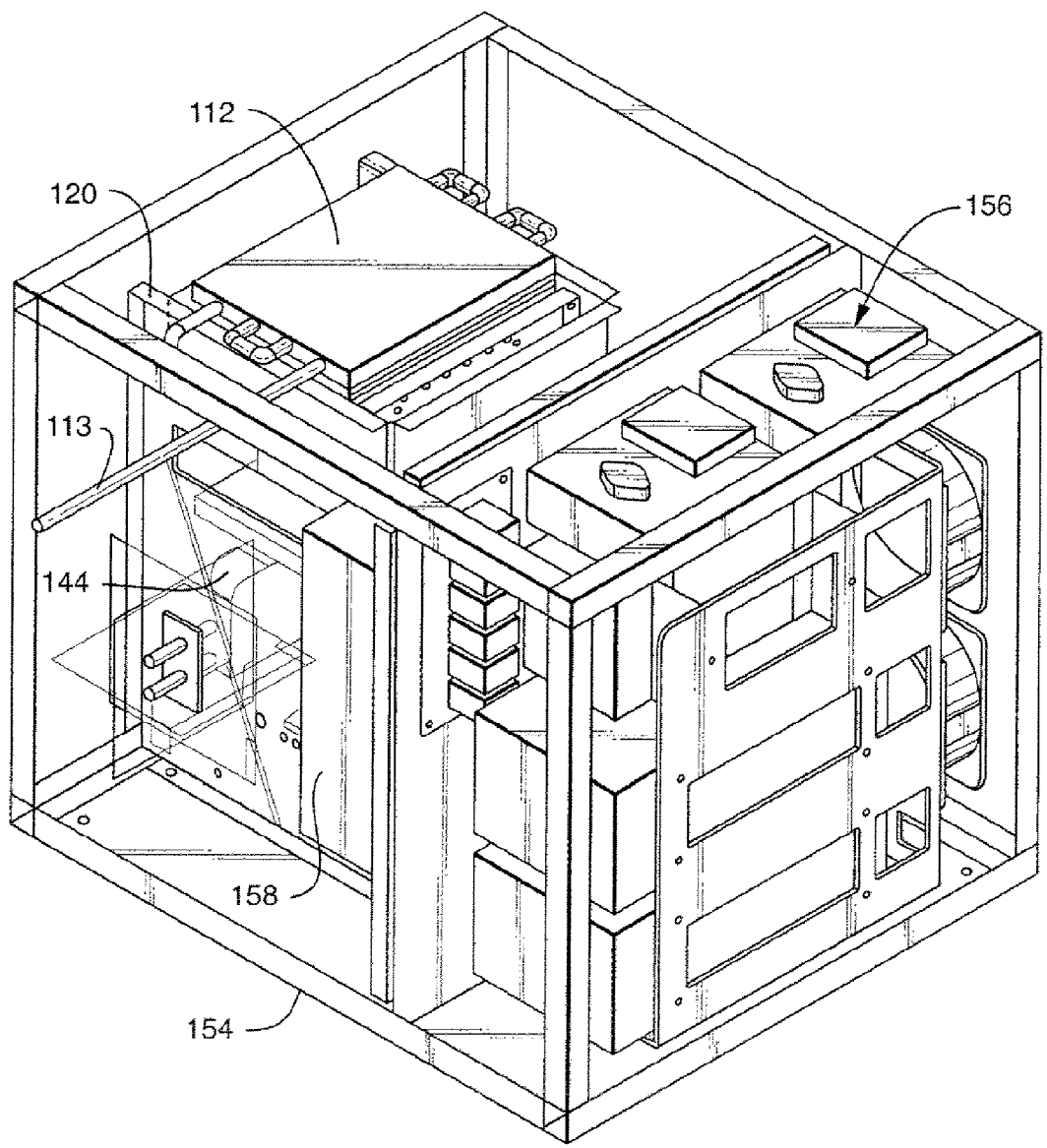
FIG. 11 shows an internal view of the assembly block diagram according to one embodiment of the present invention.

Referring to FIGS. 9-11, some other features that may be included with the present system are a lower control plate 142. The lower control plate 142 rests underneath the shield control modules 124. In the embodiment shown in FIG. 9, the lower control plate 142 is supported on a seat lift assembly 144. The seal lift assembly 144 in FIG. 9 includes a platform 148 coupled to a pneumatic lift 150. Between the platform 148 and the lower control plate 142 are one or more spacers 146. In this embodiment, the lower control plate 142 is a thick aluminum plate, the platform 148 is another thick aluminum plate, and the spacers 146 are aluminum rod standoffs. It is noted that other types of lifts could also be utilized in connection with the present system, as would be apparent to one skilled in the art. For example, the lifting could be accomplished by a hydraulic jacking mechanism, a scissors jack, a screw jack, a chain or belt drive. As appreciated by one skilled in the art, there are numerous mechanisms that could be employed to lift the adiabatic shield 122, such that the liquid samples placed in wells 128 are brought into communication with the sensor pins 102 and that the well seal gasket 118 is compressed to complete the sealing of the sample wells. For example, in one embodiment, the spacers 146 and platform 148 could be eliminated and the pneumatic lift 150 could directly raise the lower control plate 142. However, it can be advantageous to keep the additional pieces and resultant air space simply to provide a thermally stable environment (akin to the function of the heat sink 112 discussed above).

In some embodiments, it may even be desirable to have more than one heat sink 112—for example, a heat sink could be placed on the bottom as well as the top of the system 100. As seen in FIS. 9 and 10, the system 100 can also be encased in an enclosure 152. The enclosure 152 is made of sheet aluminum. The enclosure could be made of from other sheet, pressed or molded materials, including, steel, stainless steel, plastic, or fiberglass. In the present embodiment the enclosure is screwed to and supported and a chassis frame 154. As would be apparent to one skilled in the art, the frame 154 could be eliminated or made of numerous materials capable of providing the necessary structural support including, but not limited to steel, stainless steel, or aluminum tube, angle, or flat metal stock or extrusions.

As seen in FIG. 11, the enclosure 152 can also house power supplies 156, as well as a shield 158 for electro-magnetic-field (EMF) shielding of the signal processing electronics (not shown). The EMF shield in the present embodiment is a grounded copper enclosure but could be made from other materials including but not limited to mu metal. The shield 158 helps to keep out stray interfering signals from power lines, telephone lines, radio and TV transmissions, microwave ovens, and wireless devices such as mobile phones, etc.

Figure 12:
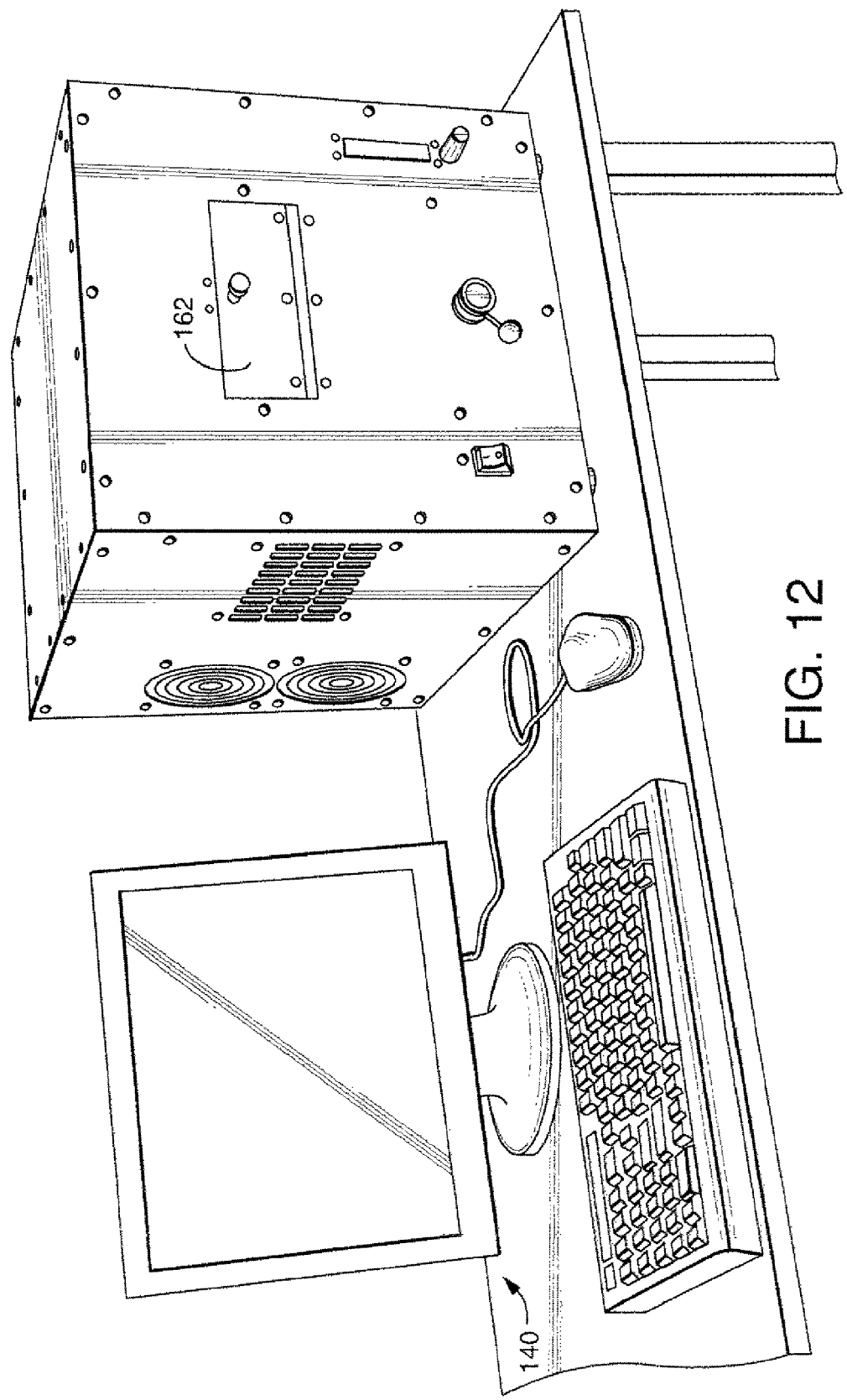
FIG. 12 shows the outside of the well array according to one embodiment of the present invention.

The operation of the present system, according to one embodiment, would be as follows: A user would place a sample 160 in one or more wells 128 of the 96 well plate 120. It is noted again that one of the advantages of the present system is its ability to utilize the sample trays and robotics of the 96 well configuration—which are in use in other assay applications, but heretofore unused in calorimetric science. The well plate 120 is then placed into the corresponding openings 134 in the adiabatic shield 122. In one embodiment, the well plates 120 are introduced through a sample tray access 162 (FIG. 12). Once the well plate 120 is placed, the access 162 is closed, and the user raises the pneumatic lift 150, which in turn raises the platform 148, which in turn raises the adiabatic shield 122.

As the samples 160 resting in the adiabatic shield 122 rise, the sensor pins 102 press down through the membranes 130 of the well seal gasket 118, and into the liquid samples contained in the sample wells 128 and corresponding samples 160. The thermal environment surrounding the samples 160 is then manipulated. For example, as noted above, the heat sink 112 can be maintained at a constant temperature by means of the coolant line 113. The same temperature would be maintained by the air space located beneath the lower control plate 142.

The scan block 110 is then heated to the desired temperature by the scan control modules 114. This heat is transferred, albeit imperfectly, through the temperature control modules 116 (also referred to as the $\Delta T$ control modules) into the calorimeter block 106. The temperature control modules 116 also directly heat the calorimeter block 106. In those embodiments containing two stages of the calorimetric block 106—i.e. stage I 108 and stage II 107—the temperature control modules 116 are in communication with (and consequently transfer heat to) stage I. Between stage I and stage II, the dampening material 109 helps to reduce thermal noise resulting from inconsistencies in heat flow that can arise from a variety of factors. The use of the temperature control modules 116 is also a means whereby a stable thermal environment can be created, with very little noise that could compromise the analytical results. The control of the temperature at the sample well level and in the vicinity of the sensor pins is maintained by several levels of increasingly finer control employing both active and passive mechanisms. The $1^{st}$ level of control is the control of the scan block 110 temperature which results from the application of heat (from the scan control modules 114) to achieve a controlled temperature and temperature change rate for the calorimeter assembly. The $2^{nd}$ level of control is that the temperature of stage I of the calorimeter block is maintained to be the same temperature as the scan block by the application of small amounts of additional heat from the $\Delta T$ control modules 116. Both of these first two control steps are accomplished using well known proportional integrated differential (PID) control strategies to achieve the desired temperature scan rate for the scan block and to maintain the stage I calorimeter block temperature at the same temperature as the scan block. Both of these feedback control processes introduce signal noise as the control set points are overshot in both directions. The next level of control is passive in that the stage II calorimeter block sees an average temperature for the stage I block. This averaging is accomplished by the passive (and slowed down) response that results from the dampened coupling of the two calorimeter blocks through the dampening material 109 that separates the two calorimeter blocks 106 and 108. The objective of both the active and passive control elements is to scan the temperature of the samples so that the energetics of temperature induced chemical reactions taking place in the samples 160 can be detected without interference form temperature (and heat flow) fluctuations from environmental or instrument artifact sources. Thus, the heat sensors 104 are in a substantially thermally stable environment. From the other end of the system 100, the adiabatic shield 122 is concurrently heated to substantially the same temperature as the scan block 110. Thus, the adiabatic shield 122, the sample plate 120, the samples 160 therein, the sensor pins 102, and the heat sensors 104 can all simultaneously be brought to substantially the same temperature.

Under such circumstances, a user can generate a variety of data. For example, the user could determine changes in the thermal stability of drug biotargets (e.g. receptors, proteins and nucleic acids) in the presence or absence of potential drug compounds (or ligands) placed into the sample wells along with the biotarget in dilute solution 128. By simultaneously and uniformly increasing the heat to the adiabatic shield 122, as well as the calorimeter block 106, both the samples 160 and the sensors 104 are in the same thermal environment. This allows the user to detect heat capacity changes in sample solutions which are the result of the thermal unfolding (denaturation) of the biotarget molecules and also the thermal energy of the receptor/ligand interactions (drug binding or release). Even more useful, the present system allows this to conceivably be done on 96 samples at once.

Of course, this is just one possible application of the present system, and numerous other uses to which it may be put include, but are not limited to, a diagnostic application in which the proteomics (or protein distribution) in a suitable biological fluid (e.g. blood, urine, peritoneal fluid, spinal fluid, amniotic fluid, saliva) is sensed in the array DSC by a characteristic thermal denaturation profile and with reference to an established database used to diagnose disease.

Variations of the Present Invention

In certain embodiments, the scan block 110 could be in direct communication with the control modules 116 and primary calorimeter block 106. In certain embodiments the sensor array could be a monolithic design instead of the 96 individually place sensors 104. In certain embodiments the sensor array could have different geometry and have 384, 1536, or more sensors in the obvious high throughput screening configurations used in other 96 well format biotech applications. In certain embodiments the measurement assembly could be placed in a vacuum. In certain embodiments the component layout, frame, and skin assemblies could be significantly varied to achieve a more compact overall design.

What is claimed is:

1. A calorimeter array comprising:
   a) one or more scan control modules;
   b) a scan block in thermal communication with the scan control modules;
   c) one or more temperature control modules;
   d) a two-stage calorimetric block having first and second stages in thermal communication with the temperature control modules, said two-stage calorimetric block comprising a passive low thermal conductivity dampening layer between the first and second stages of the two-stage calorimetric block;
   e) an array of heat flow sensors coupled to the two-stage calorimetric block;
   f) an array of sensor pins in thermal communication with the array of heat flow sensors, said array of sensor pins corresponding to the array of heat flow sensors, and said array of sensor pins configured to fit into a well plate having a corresponding array of sample wells, wherein the sensor pins are configured to be inserted into the sample wells;
   g) an adiabatic shield; and
   h) one or more shield control modules in thermal communication with the adiabatic shield.

2. The calorimeter array of claim 1, wherein temperature gradients in the calorimeter block are minimized using the adiabatic shield, said adiabatic shield comprising a metallic block made of a high thermal conductivity and high heat capacity material, having an array of holes dimensioned and located such that the array of sensor pins corresponds to the array of holes in the metallic block.

3. The calorimeter array of claim 1, wherein the array of heat flow sensors comprises 96 heat flow sensors, and wherein each of the 96 heat flow sensors may be used in either a single ended or differential mode when paired with any other sensor in the array or with several other specifically located sensors in the array.

4. The calorimeter array of claim 1, wherein the adiabatic shield is capable of receiving a 96 well sample plate.

5. The calorimeter array of claim 1, further comprising a 96 well sample plate, wherein each of the 96 wells in the 96 well sample plate is sealed to a pressure adequate to contain water at temperatures to 120° C.

6. The calorimeter array of claim 1, further comprising a sample well plate, a sealing gasket positioned over the sample well plate and a lift assembly capable of generating an applied sealing force to the sealing gasket adequate to prevent loss of water through evaporation or boiling at temperatures to 120° C.

7. A calorimeter array comprising:
   a) one or more scan control modules;
   b) a scan block in thermal communication with the scan control modules;
   c) one or more temperature control modules;
   d) a two-stage calorimetric block in thermal communication with the temperature control modules;
   e) a passive low thermal conductivity dampening layer between the two stages of the two-stage calorimetric block;
   f) an array of heat flow sensors coupled to the calorimetric block; and
   g) an array of sensor pins, wherein each of the sensor pins is in thermal communication with a corresponding heat flow sensor in the array of heat flow sensors.

8. The calorimeter array of claim 7, wherein the two-stage calorimeter block has a first stage and a second stage, and wherein the temperature of the first stage is actively controlled and the temperature of the second stage is passively controlled.

9. The calorimeter array of claim 7, wherein the dampening layer comprises an aluminum layer and a silicone rubber layer.

10. The calorimeter array of claim 7, further comprising a well plate comprising an array of sample wells covered by one or more protective membranes, wherein the array of sensor pins is configured to puncture through the protective membranes and enter the array of sample wells.

11. A calorimeter array comprising:
   a) one or more scan control modules;
   b) a scan block in thermal communication with the scan control modules;
   c) one or more temperature control modules;
   i) a two-stage calorimetric block in thermal communication with the temperature control modules, said two-stage calorimetric block comprising a passive low thermal conductivity dampening layer between the first and second stages of the two-piece calorimetric block;
   d) an array of heat flow sensors coupled to the calorimetric block;
   e) a matching array of sensor pins in thermal communication with the heat flow sensors; and
   f) a well plate comprising a matching array of sample wells containing liquid samples, wherein each of the sensor pins is configured to fit into a corresponding sample well in the array of sample wells.

12. The calorimeter array of claim 11, further comprising a well seal gasket having a matching array of channels.

13. The calorimeter array of claim 12, further comprising one or more protective membranes positioned over one or more of the channels.

14. The calorimeter array of claim 13, configured such that when the sample wells are raised up, the sensor pins puncture through the protective membranes.

15. The calorimeter array of claim 11, further comprising an adiabatic shield comprising a metallic block made of a high thermal conductivity and high heat capacity material.

* * * * *